(12) United States Patent
Rubin

(10) Patent No.: US 6,672,873 B2
(45) Date of Patent: *Jan. 6, 2004

(54) IMPLEMENT AND METHOD FOR DETERMINING PRESENCE OF MOISTURE IN A ROOT CANAL

(76) Inventor: Gregory Rubin, 24704 Calle Conejo, Calabasas, CA (US) 91302

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 80 days.

This patent is subject to a terminal disclaimer.

(21) Appl. No.: 10/000,373

(22) Filed: Oct. 30, 2001

(65) Prior Publication Data

US 2003/0008264 A1 Jan. 9, 2003

Related U.S. Application Data

(63) Continuation-in-part of application No. 09/899,483, filed on Jul. 4, 2001, now Pat. No. 6,482,009.

(51) Int. Cl.$^7$ .............................. A61C 5/02; A61C 3/00
(52) U.S. Cl. ...................................... 433/224; 433/141
(58) Field of Search ........................... 433/81, 141, 224

Primary Examiner—John J. Wilson
(74) Attorney, Agent, or Firm—Robert J. Schaap

(57) ABSTRACT

A method of and device for testing for conditions, particularly moisture conditions, in root canals and for drying the root canal. In accordance with the method, a small pointed implement in the nature of a rolled piece of paper having pH indicator on the tip thereof is inserted into the root canal. The pH indictor, by change of color, will present information as to whether or not any moisture is present in the canal and, secondly, whether or not the moisture is a positive pH or negative pH.

15 Claims, 1 Drawing Sheet

IMPLEMENT AND METHOD FOR DETERMINING PRESENCE OF MOISTURE IN A ROOT CANAL

RELATED APPLICATION

This application is a continuation-in-part of my co-pending U.S. patent application Ser. No. 09/899,483, filed July 4, 2001, now U.S. Pat. No. 6,482,009 for Root Canal Testing Implement and Method.

BACKGROUND OF THE INVENTION

1. Field of the Invention

This invention relates in general to certain new and useful improvements in methods and devices for testing the condition of a tooth root canal and, more particularly, to a simple and easy test for determining whether there is moisture present in the root canal of a tooth, prior to sealing the root canal with a sealing material.

2. Brief Description of Related Art

Although the science relating to dental procedures has increased dramatically over the years, there remains some relatively simple but yet perplexing problems which still confront the dentist in the performing of and preparation of root canals. It is well established that a root canal must be perfectly dry and contain no presence of moisture whatsoever before any filling can be introduced into the root canal. In some cases, a dentist will attempt to use a small diameter cotton swab and attempt to wipe the wall of the canal with this cotton swab or use paper points, as hereinafter described.

The tooth canal is usually curved and, moreover, of a relatively small cross-sectional size. Consequently, a swab is not capable of being inserted to any reasonable depth within the root canal.

Many dentists will attempt to use air from an air jet supplied from a pressurized source of air. However, the air in this pressurized source frequently does contain a small amount of moisture and the moisture from that air can actually condense in the root canal of the tooth, thereby militating against the use of air.

There are presently devices known as paper points which are frequently used by dentists in an attempt to wipe the wall of the root canal, particularly at the lower depths thereof. In this case, paper, typically of a triangular shape, is rolled by a manufacturer of these paper points into small thin rod-like elements having a point at an end adapted for insertion into the canal of the tooth. In this case, the paper itself is somewhat moisture absorbent and tends to absorb some of the moisture which may be present in the root canal of the tooth. However, the drying of the canal with a paper point is frequently not sufficient. One of the more important problems arising from the use of these paper points is the fact that there is no effective and convenient means to determine whether or not moisture is still present in the tooth, even after the attempts to remove all moisture. As a result, some dentists will attempt to continue with the filling of the tooth, even though moisture could be present and this may further result in additional deterioration, if not infection, of the tooth and poor treatment prognosis.

In some cases, a dentist will attempt to take a paper point, insert the same into a root canal of a tooth, withdraw the paper point and attempt to bend the paper point on a dental tray or other surface. This rudimentary test is designed to determine if moisture is present which had been absorbed in the paper point causing the same to bend easily. Obviously, this is, at very best, a rudimentary test and certainly is not effective to determine if all moisture has effectively been removed.

Frequently, the dentist is unable to insert the swab to the lowest depth of the canal and this is the point at which water would tend to accumulate. Consequently, there is no effective and reliable means for insuring that all moisture has been removed from the canal before any further procedure takes place.

One of the problems associated with root canals is the presence of infection. When the pulp chamber of the tooth is opened, there is a tendency for bacterial growth to occur within the open cavity of the tooth. Frequently, until this bacterial growth has at least caused some damage or associated pain and discomfort, the bacteria remains undetected. Consequently, it is quite important for the dentist to be able to detect the presence of any bacterial condition which may exist in the root canal.

It would therefore be desirable to provide a device which is accurate and reliable and of low cost for determining whether moisture may be present in the root canal of a tooth. In addition, it would also be desirable to provide an inexpensive and effective means which could aid in determining bacterial presence.

OBJECTS OF THE INVENTION

It is, therefore, one of the primary objects of the present invention to provide a method for insuring that all moisture in a root canal of a tooth has been removed.

It is another object of the present invention to provide a method for aiding in determining the presence of any infected body fluid in a root canal.

It is also an object of the present invention to provide a device for determining whether or not moisture is present in a root canal of a tooth by a simple visual color change test.

It is yet another salient object of the present invention to provide a device of the type stated which can be constructed at a relatively low unit cost and which is highly effective in operation and highly reliable in use.

With the above and other objects in view, my invention resides in the novel features of form, construction, arrangement, and combination of parts as presently described and pointed out in the claims.

BRIEF SUMMARY OF THE INVENTION

The present invention relates in general terms to a device and a method for testing whether or not moisture is present in a root canal of a tooth and for also drying the canal to insure removal of all moisture.

The present invention relies upon a relatively small diameter implement, such as a paper point of the type frequently used by dentists. In this case, a moisture responsive color change indicator is impregnated into the lower portion or apical region of the paper point in order to determine whether or not moisture is present in the root canal of the tooth. In place of a paper point, it is also possible to use a relatively small diameter implement, such as a very thin diameter implement, which is impregnated with a pH indicator at the lower end thereof. However, it is necessary for the device to be somewhat bendable in order to conform to the curvature of the root canal in many teeth.

By inserting a paper point or similar implement into the root canal of the tooth, if moisture is present, the color change indicator impregnated into the lower end of the paper point or other implement will be actuated by moisture and change colors. In this way, the dentist will be immediately advised of the presence of moisture by virtue of the color change.

If moisture is detected, the dentist can thereupon attempt to use some other means for drying out the root canal as, for example, additional paper points to absorb any remaining moisture in the root canal. Thereafter, the dentist or other technician can insert yet another paper point with a moisture sensitive color change indicator on the lower end in order to determine if all moisture has been removed. The paper point will not change color if there is no other moisture present in the root canal.

In addition to the foregoing, it is sometimes necessary to determine whether or not infected body fluids may be present in a root canal. If the implement which is inserted in the root canal shows the presence of blood, then the dentist or technician is immediately advised of a certain condition which must be treated. Otherwise, if the moisture sensitive color change indicator shows a color change, this may provide very basic information to the dentist or other dental practitioner as to whether or not bacterial growth may be present. The use of a color change indicating test is not effective to actually determine if of bacterial growth is present. However, it could provide some basis as to whether or not infection is present.

The present thereby provides both a method for detecting the presence of moisture. The device in the nature of a pre-impregnated paper point can be produced at a very low unit cost and is highly reliable in its operation. In addition, the method of the invention can be performed with a minimum amount of manual attention and can also be performed very quickly.

This invention possesses many other advantages and has other purposes which may be made more clearly apparent from a consideration of the forms in which it may be embodied. These forms are shown in the drawings forming a part of and accompanying the present specification. They will now be described in detail for purposes of illustrating the general principles of the invention. However, it is to be understood that the following detailed description and the accompanying drawings are not to be taken in a limiting sense.

BRIEF DESCRIPTION OF THE DRAWINGS

Figure 1:
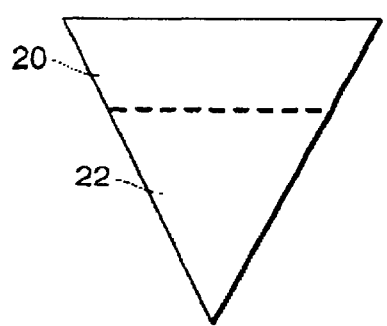
Figure 2:
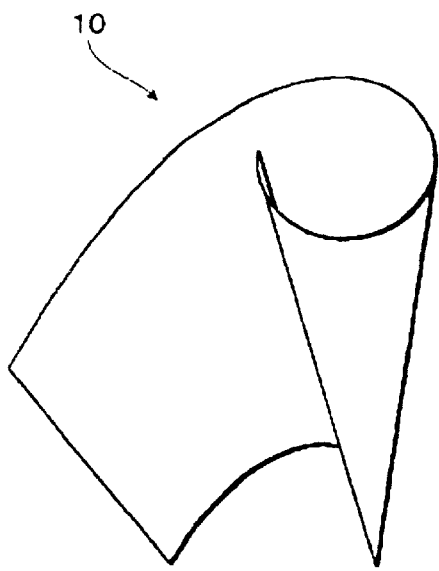
Figure 3:
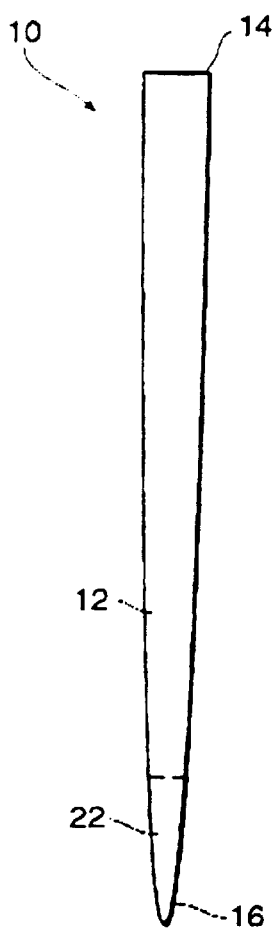
Figure 4:
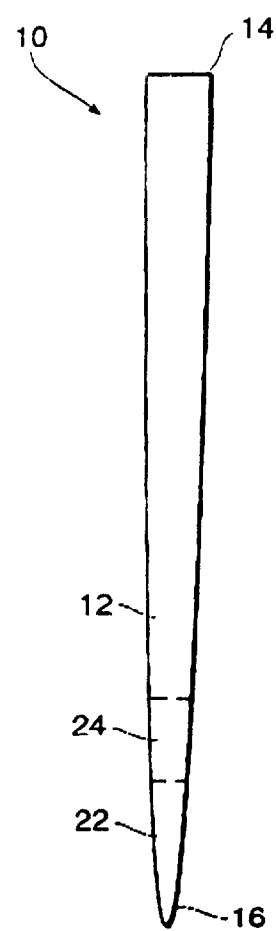

Having thus described the invention in general terms, reference will now be made to the accompanying drawings in which:

FIG. 1 is a plan view of a piece of absorbent paper in triangular shape which is used to make the paper point of the present invention;

FIG. 2 is a perspective view showing the piece of absorbent paper of FIG. 1 being rolled into a paper point;

FIG. 3 is a side elevational view of a paper point used in accordance with the present invention; and FIG. 4 is a side elevational view of a modified form of paper point which may be used in accordance with the present invention.

DETAILED DESCRIPTION OF A PREFERRED EMBODIMENT

Referring now in more detail and by reference characters to the drawings, FIG. 3 illustrates one device 10 which may be used for testing for the presence of moisture in a root canal of a tooth. The device 10 generally comprises an elongate paper point having a shank 12 and an enlarged upper end 14 for engagement by the hands of a user or an instrument holder to engage the shank 12, as well as a pointed lower end or tip 16 for insertion into a root canal.

The paper point of the invention is preferably formed from a piece of triangularly shaped absorbent paper 20, as shown in FIG. 1, and which is rolled into a paper point, such as the paper point 10 in the manner as initially shown in FIG. 2. The paper point of the invention at its lower point or tip portion is preferably pre-impregnated at a place of manufacturing with a moisture responsive color change indicator region 22, as best shown in both FIGS. 1 and 3 of the drawings. In other words, the color change indicator material is incorporated in the paper at a place of manufacture. Otherwise, the composition could be provided with the paper points for the dentist or other practitioner to impregnate the composition into the paper.

The moisture testing device of the invention is therefore formed of a rolled paper material but which is still sufficiently durable to be inserted into a canal of a tooth. Inasmuch as the device is a throw away device, that is, after it has been used on one occasion, it is disposable, and any light weight and even relatively degradable material can be used for this purpose. It is important to be able to ensure that a moisture responsive color change indicator can be applied to the lower end of the shank 12.

By reference to FIG. 4, it can observed that there are a pair of color change indicators 22 and 24 which are applied to the lower end of the shank 12. In this case, the color change indicators can be initially liquid and impregnated into the lower end of the shank 12. Otherwise, they could be applied and retained on the lower end of the shank by any conventional means. For that matter, small strips of paper containing an impregnated pH indicator could be applied to the lower end of the shank 12.

A dentist or technician can take a small piece of paper, roll it into a thin small diameter roll having a very small diameter lower end. The roll of paper can then be dipped into a liquid color change indicator to impregnate the paper roll at least at the tip. Time must be allotted to any liquid carrier on the paper roll to dry.

In my co-pending U.S. patent application identified above, there is a described a process and device which uses a pH indicator for creating a color change responsive to a basic or acidic condition of a tooth. This is effective to some slight extent in determining the presence of bacterial growth. Nevertheless, with the presence of liquid, the pH is never 7.0 and, hence, a pH indicator is operative.

It has been found in connection with the present invention that it is also possible and, indeed, highly effective to use dyes, such as food dyes. In this case, any pharmaceutically non-toxic dye, such as those conventional food dyes which are already approved as food additives, can be used. Only those dyes which have been approved by the Food and Drug Administration and have been provided with an FD&C number acceptable for use. Specifically, some the dyes which may be used are Yellow No. 1, Yellow No. 5, Red No. 4 and Red No. 5. One of the preferred dyes which may be used in accordance with the present invention is that dye known as Blue No. 1. Any of the color dyes which are used must naturally be capable of changing color in response to presence of moisture. Thus, a dye which is capable of changing color in the presence of moisture is referred to herein as a "moisture responsive color change indicator".

It is also possible to use a fine powder material dusted onto the paper but which is of such fine particulate size that color is not readily apparent. Nevertheless, when introduced in water or other liquid, the color of the particulate material becomes immediately apparent. Thus, for example, a blue particulate powder could be dusted onto the paper point and impregnated in the grains of the paper and only becomes visually apparent when subjected to the presence of moisture. Nevertheless, inasmuch as this type of action only makes the color readily apparent, this material is also referred to herein as a color change indicator.

The amount of the dye which is applied is not critical in accordance with the invention, although it must be at least sufficient to provide a clear color change to enable the dentist or other dental practitioner to determine whether or not moisture is present by a color change. It may also be used to provide a very rough indication as to whether or not bacterial growth may be present.

The method of the present invention can also be used in a very low cost manner by allowing a dental practitioner to roll up a piece of paper with a lower pointed end. Again, drying time for evaporation of any liquid carrier must be allowed. The practitioner would then impregnate that piece of paper with a color change indicator.

Thus, there has been illustrated and described a unique and novel device and method which are capable of detecting presence of moisture in a root canal of a tooth and which thereby fulfills all of the objects and advantages which have been sought. It should be understood that many changes, modifications, variations and other uses and applications which will become apparent to those skilled in the art after considering the specification and the accompanying drawings. Therefore, any and all such changes, modifications, variations and other uses and applications which do not depart from the spirit and scope of the invention are deemed to be covered by the invention.

I claim:

1. A method for detecting whether moisture is present in a root canal of a tooth, said method comprising:
    a) inserting an implement containing a color change indicator which changes color in response to presence of moisture into the root canal of a tooth; and
    b) withdrawing the implement from the canal of the tooth and determining whether the indicator has changed color which thereby provides indication of the presence of moisture.

2. The method of claim 1 further characterized in that the implement comprises an elongate paper roll having a lower pointed end thereof with the color change indicator in proximity to that lower pointed end.

3. The method of claim 1 further characterized in that said method comprises rolling a piece of paper to a sharp point and applying at least one pH indicator in proximity to that sharp point of the implement.

4. The method of claim 1 further characterized in that said color change indicator is Red Dye No. 4.

5. The method of claim 1 further characterized in that said color change indicator is Yellow No. 2.

6. The method of claim 1 further characterized in that said color change indicator is Yellow No. 5.

7. The method of claim 1 further characterized in that said color change indicator is Blue No. 1.

8. An implement for determining whether or not moisture is present in a root canal of a tooth and whether that moisture may cause a color change to show presence of moisture, said device comprising:
    a) an elongate rod like member having an enlarged upper end for engagement by the fingers of a user;
    b) a tip at the lower end of said rod like member and having a cross-sectional size such that it will fit into a root canal of a tooth; and
    c) a color change indicator on said rod like member adjacent the lower end thereof for indicating the presence of moisture in a root canal of a tooth by a color change when the implement in inserted in a root canal and shows a change of color.

9. The implement of claim 8 further characterized in that said implement is a rolled piece of paper.

10. The implement of claim 8 further characterized in that the implement has a tapered lower edge.

11. The implement of claim 8 further characterized in that a pair of color change indicators are provided on the lower end of the implement in proximity to the tip thereof.

12. An implement for determining whether or not moisture is present in a root canal of a tooth and whether that moisture may have a certain pH associated therewith, said device comprising:
    a) an elongate rod like member having an enlarged upper end for engagement by the fingers of a user;
    b) a tip at the lower end of said rod like member and having a cross-sectional size such that it will fit into a root canal of a tooth; and
    c) a section of the lower end of said rod like member adjacent the tip which is capable of being inserted into a root canal of a tooth and which lower end is responsive to the presence of moisture and will change color in the presence of moisture and thereby indicates to a user the presence of moisture in a root canal of a tooth when the implement in inserted therein.

13. The implement of claim 12 further characterized in that said implement is a rolled piece of paper.

14. The implement of claim 12 further characterized in that the implement has a tapered lower end.

15. The implement of claim 12 further characterized in that the tip is a relatively sharp pointed tip.

* * * * *